United States Patent
Knodel et al.

(10) Patent No.: US 9,408,605 B1
(45) Date of Patent: Aug. 9, 2016

(54) SINGLE-TRIGGER CLAMPING AND FIRING OF SURGICAL STAPLER

(75) Inventors: Bryan D. Knodel, Flagstaff, AZ (US); Yaeer E. Lev, Rolling Hills Estates, CA (US)

(73) Assignee: Cardica, Inc., Redwood City, CA (US)

( * ) Notice: Subject to any disclaimer, the term of this patent is extended or adjusted under 35 U.S.C. 154(b) by 956 days.

(21) Appl. No.: 13/451,344

(22) Filed: Jul. 12, 2012

(51) Int. Cl.
| | |
|---|---|
| *A61B 17/068* | (2006.01) |
| *A61B 17/072* | (2006.01) |
| *A61B 17/29* | (2006.01) |
| *A61B 17/00* | (2006.01) |

(52) U.S. Cl.
CPC . *A61B 17/07207* (2013.01); *A61B 2017/00367* (2013.01); *A61B 2017/2923* (2013.01)

(58) Field of Classification Search
CPC ............... A61B 17/07207; A61B 2017/2917; A61B 2017/2923; A61B 2017/292; A61B 2017/2922; A61B 2017/2915; A61B 2017/00367; A61B 2017/00407; A61B 2017/2919
See application file for complete search history.

(56) References Cited

U.S. PATENT DOCUMENTS

| | | | |
|---|---|---|---|
| 2,127,665 A | 8/1938 | Leslie | |
| 3,581,551 A | 6/1971 | Wilkinson | |
| 3,650,453 A | 3/1972 | Smith, Jr. | |
| 3,675,688 A | 7/1972 | Bryan et al. | |
| 3,717,294 A | 2/1973 | Green | |
| 3,837,555 A | 9/1974 | Green | |
| 3,899,914 A | 8/1975 | Akiyama | |
| 3,955,581 A | 5/1976 | Spasiano et al. | |
| 4,043,504 A | 8/1977 | Hueil et al. | |
| 4,086,926 A | 5/1978 | Green et al. | |
| 4,127,227 A | 11/1978 | Green | |
| 4,228,895 A | 10/1980 | Larkin | |
| 4,275,813 A | 6/1981 | Noiles et al. | |
| 4,475,679 A | 10/1984 | Fleury, Jr. | |
| 4,523,707 A | 6/1985 | Blake, III et al. | |
| 4,556,058 A | 12/1985 | Green | |
| 4,589,416 A | 5/1986 | Green | |
| 4,633,861 A | 1/1987 | Chow et al. | |
| 4,655,222 A | 4/1987 | Florez et al. | |
| 4,719,917 A | 1/1988 | Barrows et al. | |
| 4,762,260 A | 8/1988 | Richards et al. | |
| 4,969,591 A | 11/1990 | Richards et al. | |

(Continued)

FOREIGN PATENT DOCUMENTS

| | | |
|---|---|---|
| EP | 1238634 | 9/1994 |
| EP | 1464287 | 10/2004 |

(Continued)

OTHER PUBLICATIONS

International Search Report, PCT/US2013/034593, mailed Jul. 18, 2013.
Gong, Shao W., "Perfectly flexible mechanism and integrated mechanism system design", *Mechanism and Machine Theory* 39 (2004), (Nov. 2004), 1155-1174.

(Continued)

*Primary Examiner* — Andrew M Tecco
(74) *Attorney, Agent, or Firm* — Womble Carlyle Sandridge & Rice LLP

(57) ABSTRACT

An exemplary surgical apparatus includes an end effector; and a handle operationally connected to the end effector, the handle including a trigger and a mode button; where the mode button is first in a neutral position in which actuation of the trigger causes the end effector to move to a clamped configuration; and where the mode button is movable laterally to a second position in which actuation of the trigger causes the end effector to deploy staples.

16 Claims, 14 Drawing Sheets

(56) References Cited

U.S. PATENT DOCUMENTS

| | | |
|---|---|---|
| 4,978,049 A | 12/1990 | Green |
| 5,156,315 A | 10/1992 | Green et al. |
| 5,170,925 A | 12/1992 | Madden et al. |
| 5,192,288 A | 3/1993 | Thompson et al. |
| 5,242,457 A | 9/1993 | Akopov et al. |
| 5,269,792 A | 12/1993 | Kovac et al. |
| 5,307,976 A | 5/1994 | Olson et al. |
| 5,413,272 A | 5/1995 | Green et al. |
| 5,415,334 A | 5/1995 | Williamson, IV et al. |
| 5,456,400 A | 10/1995 | Shichman et al. |
| 5,476,206 A | 12/1995 | Green |
| 5,507,776 A | 4/1996 | Hempel |
| 5,527,319 A | 6/1996 | Green et al. |
| 5,547,117 A | 8/1996 | Hamblin et al. |
| 5,547,474 A | 8/1996 | Kloeckl et al. |
| 5,553,765 A | 9/1996 | Knodel et al. |
| 5,620,289 A | 4/1997 | Curry |
| 5,626,585 A | 5/1997 | Mittelstadt et al. |
| 5,630,541 A | 5/1997 | Williamson, IV et al. |
| 5,655,698 A | 8/1997 | Yoon |
| 5,662,260 A | 9/1997 | Yoon |
| 5,692,668 A | 12/1997 | Schulze et al. |
| 5,810,855 A | 9/1998 | Rayburn et al. |
| 5,816,471 A | 10/1998 | Plyley et al. |
| 5,855,311 A | 1/1999 | Hamblin et al. |
| 5,871,135 A | 2/1999 | Williamson IV et al. |
| 5,875,538 A | 3/1999 | Kish et al. |
| 5,894,979 A | 4/1999 | Powell |
| 5,918,791 A | 7/1999 | Sorrentino et al. |
| 5,964,774 A | 10/1999 | McKean et al. |
| 6,264,087 B1 | 7/2001 | Whitman |
| 6,306,149 B1 | 10/2001 | Meade |
| 6,391,038 B2 | 5/2002 | Vargas et al. |
| 6,419,682 B1 | 7/2002 | Appleby et al. |
| 6,443,973 B1 | 9/2002 | Whitman |
| 6,478,804 B2 | 11/2002 | Vargas et al. |
| 6,592,597 B2 | 7/2003 | Grant et al. |
| 6,602,252 B2 | 8/2003 | Mollenauer |
| 6,716,232 B1 | 4/2004 | Vidal et al. |
| 6,817,508 B1 | 11/2004 | Racenet |
| 6,843,403 B2 | 1/2005 | Whitman |
| 7,025,747 B2 | 4/2006 | Smith |
| 7,055,730 B2 | 6/2006 | Ehrenfels et al. |
| 7,055,731 B2 | 6/2006 | Shelton, IV et al. |
| 7,083,075 B2 | 8/2006 | Swayze et al. |
| 7,097,089 B2 | 8/2006 | Marczyk |
| 7,111,768 B2 | 9/2006 | Cummins et al. |
| 7,121,446 B2 * | 10/2006 | Arad ............... A61B 17/07207 227/175.4 |
| 7,128,253 B2 | 10/2006 | Mastri et al. |
| 7,140,527 B2 | 11/2006 | Ehrenfels et al. |
| 7,168,604 B2 | 1/2007 | Milliman et al. |
| 7,172,104 B2 | 2/2007 | Scirica et al. |
| 7,179,267 B2 | 2/2007 | Nolan et al. |
| 7,207,471 B2 | 4/2007 | Heinrich et al. |
| 7,213,736 B2 | 5/2007 | Wales et al. |
| 7,225,963 B2 | 6/2007 | Scirica |
| 7,225,964 B2 | 6/2007 | Mastri et al. |
| 7,234,624 B2 | 6/2007 | Gresham et al. |
| 7,238,195 B2 | 7/2007 | Viola |
| 7,258,262 B2 | 8/2007 | Mastri et al. |
| 7,401,720 B1 | 7/2008 | Durrani |
| 7,434,715 B2 | 10/2008 | Shelton, IV et al. |
| 7,467,740 B2 | 12/2008 | Shelton, IV et al. |
| 7,497,865 B2 | 3/2009 | Willis et al. |
| 7,506,791 B2 | 3/2009 | Omaits et al. |
| 7,517,356 B2 | 4/2009 | Heinrich |
| 7,588,177 B2 | 9/2009 | Racenet |
| 7,604,151 B2 | 10/2009 | Hess et al. |
| 7,635,073 B2 | 12/2009 | Heinrich |
| 7,635,373 B2 | 12/2009 | Ortiz |
| 7,641,432 B2 | 1/2010 | Lat et al. |
| 7,644,848 B2 | 1/2010 | Swayze et al. |
| 7,866,527 B2 * | 1/2011 | Hall ............... A61B 17/07207 227/175.2 |
| 7,905,380 B2 * | 3/2011 | Shelton, IV ........ A61B 17/072 227/175.1 |
| 7,963,431 B2 * | 6/2011 | Scirica ............ A61B 17/07207 227/175.1 |
| 7,967,178 B2 * | 6/2011 | Scirica ............ A61B 17/07207 227/175.1 |
| 8,196,796 B2 * | 6/2012 | Shelton, IV ...... A61B 17/07207 227/175.1 |
| 8,281,973 B2 | 10/2012 | Wenchell et al. |
| 8,342,378 B2 | 1/2013 | Marczyk et al. |
| 8,424,736 B2 * | 4/2013 | Scirica ............ A61B 17/07207 227/175.1 |
| 8,534,528 B2 * | 9/2013 | Shelton, IV ...... A61B 17/07207 227/175.1 |
| 8,584,679 B2 | 11/2013 | Lowe et al. |
| 2003/0120284 A1 | 6/2003 | Palacios et al. |
| 2003/0236551 A1 | 12/2003 | Peterson |
| 2005/0184121 A1 | 8/2005 | Heinrich |
| 2006/0011699 A1 | 1/2006 | Olson et al. |
| 2006/0041273 A1 | 2/2006 | Ortiz et al. |
| 2006/0151567 A1 | 7/2006 | Roy |
| 2006/0241660 A1 | 10/2006 | Bombard et al. |
| 2006/0253143 A1 | 11/2006 | Edoga |
| 2007/0027472 A1 | 2/2007 | Hiles et al. |
| 2007/0034668 A1 | 2/2007 | Holsten et al. |
| 2007/0073341 A1 | 3/2007 | Smith et al. |
| 2007/0083234 A1 | 4/2007 | Shelton, IV et al. |
| 2007/0118163 A1 | 5/2007 | Boudreaux et al. |
| 2007/0125828 A1 | 6/2007 | Rethy et al. |
| 2007/0175950 A1 | 8/2007 | Shelton, IV et al. |
| 2008/0078807 A1 | 4/2008 | Hess et al. |
| 2008/0272175 A1 | 11/2008 | Holsten et al. |
| 2009/0145947 A1 * | 6/2009 | Scirica ............ A61B 17/07207 227/175.2 |
| 2009/0206124 A1 * | 8/2009 | Hall .................. A61B 17/07207 227/175.1 |
| 2010/0179559 A1 | 7/2010 | Walker |
| 2011/0121051 A1 * | 5/2011 | Shelton, IV ........ A61B 17/072 227/175.1 |
| 2011/0155786 A1 * | 6/2011 | Shelton, IV ...... A61B 17/07207 227/180.1 |
| 2013/0334280 A1 * | 12/2013 | Krehel ............ A61B 17/07207 227/176.1 |

FOREIGN PATENT DOCUMENTS

| | | |
|---|---|---|
| EP | 1736104 | 3/2009 |
| EP | 2082691 | 7/2009 |
| JP | 2005160933 | 6/2005 |
| RU | 2080833 | 6/1997 |
| WO | WO-81/01953 | 7/1981 |
| WO | WO-85/01427 | 4/1985 |

OTHER PUBLICATIONS

Lim, Jonas J., et al., "A review of mechanism used in laparascopic surgical instruments", *Mechanism and Machine Theory* 38, (2003), 1133-1147.

Lim, Jyue B., "Type Synthesis of a Complex Surgical Device", *Masters Thesis*, Feb. 21, 2001.

Lim, Jonas J., et al., "Application of Type Synthesis Theory to the Redesign of a Complex Surgical Instrument", *Journal of Biomechanical Engineering (124)*, (Jun. 2004),265-272.

Kolios, Efrossini et al., "Microlaparoscopy", *J. Endourology* 18(9), (Nov. 2004),811-817.

Steichen, Felicien M., et al., "Mechanical Sutures in Surgery", *Brit. J. Surg.* 60(3), (Mar. 1973),191-197.

"Notification of Transmittal of the International Search Report and the Written Opinion of the International Searching Authority", PCT/US2008/075449, (Apr. 29, 2009).

"International Search Report", PCT/US2008/075449, (Apr. 29, 2009).

"Written Opinion of the International Searching Authority", PCT/US2008/075449, (Apr. 29, 2009).

"Cardica Microcutter Implant Delivery Device 510(k), Cover Sheet, Table 10.1, "Substantial Equivalence Comparison,"and Section 12, "Substantial Equivalence Discussion"", (Oct. 18, 2010).

* cited by examiner

SINGLE-TRIGGER CLAMPING AND FIRING OF SURGICAL STAPLER

FIELD OF THE INVENTION

The invention generally relates to surgical instruments, and more specifically to the actuation of surgical instruments.

BACKGROUND

Minimally invasive surgery is performed through small incisions in the body, into which trocar ports may or may not be placed. One or more surgical instruments are inserted through each incision in order to perform the surgical procedure. In order to effectuate one of the objectives of minimally invasive surgery, which is the minimization of incisions to the body to reduce healing time and scarring, it is desirable to minimize the number of incisions made in the body. The number of incisions and their placement are determined by the particular surgical procedure to be performed and the configuration of the instruments used to carry out that procedure.

One problem encountered during the performance of surgical stapling in a minimally-invasive procedure, or even an open surgical procedure, is the need for different triggers on a surgical stapler for clamping and for staple deployment. The use of multiple triggers increases the complexity of use of, the part count of, and the size of a surgical stapler.

BRIEF DESCRIPTION OF THE DRAWINGS

The use of the same reference symbols in different figures indicates similar or identical items.

DETAILED DESCRIPTION

U.S. Pat. No. 7,954,683, issued on Jun. 7, 2011, and U.S. Pat. No. 7,988,026, issued on Aug. 2, 2011 (the "Endocutter Documents"), are herein incorporated by reference in their entirety.

Figure 1:
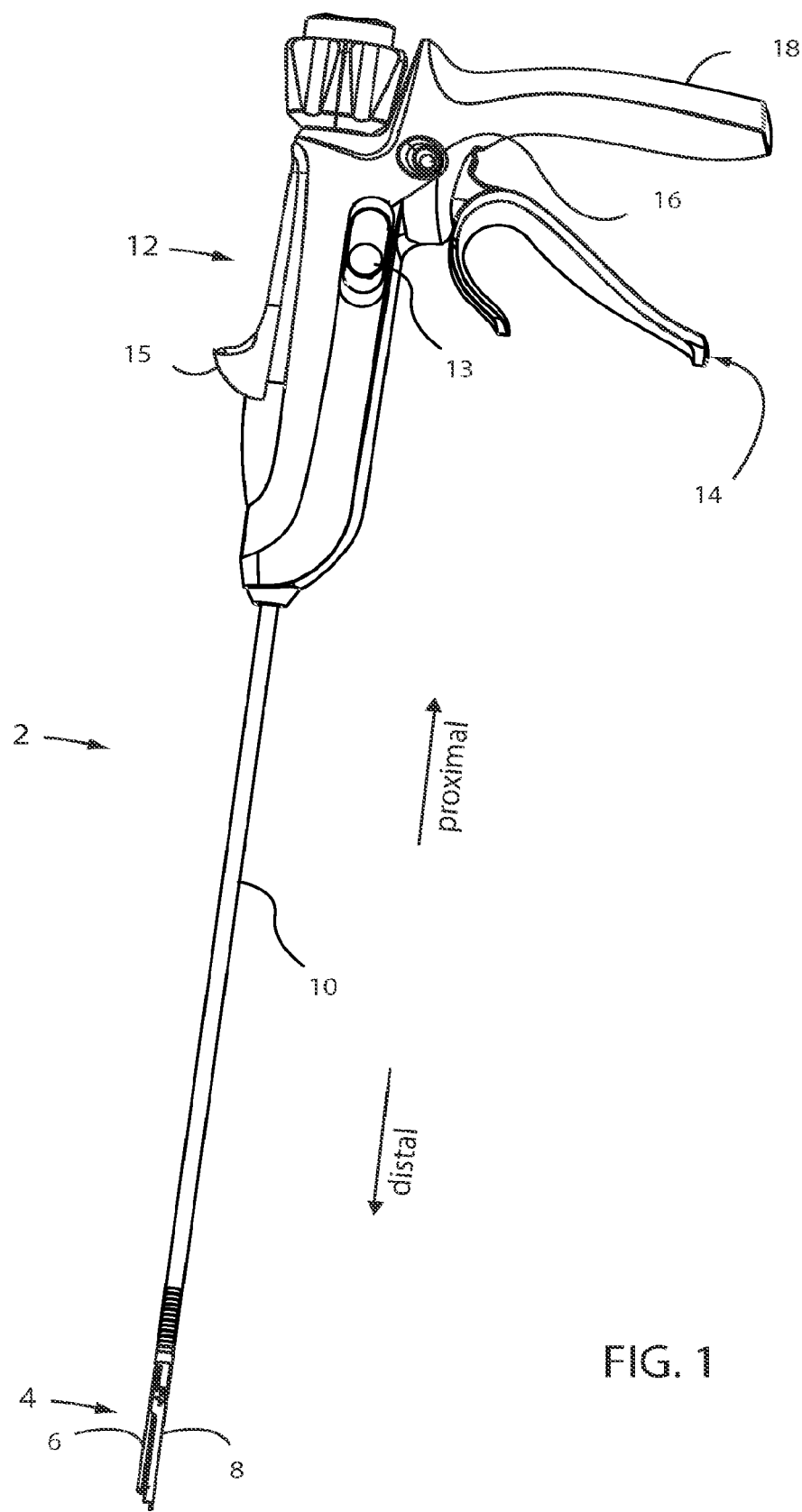
FIG. 1 is a perspective view of a surgical stapler.

Referring to FIG. 1, an exemplary surgical stapler 2 may include an end effector 4, which in turn includes a staple holder 8 and an anvil 6, where at least one of the staple holder 8 and the anvil 6 are rotatable and/or otherwise movable relative to one another. Alternately, the staple holder 8 and the anvil 6 may be directly connected to one another in any other suitable manner, if desired. The staple holder 8 and anvil 6 may be configured substantially as set forth in the Endocutter Document. As another example, the staple holder 8 may be a single-use cartridge, detachable from a remainder of the end effector 4. If so, the feeder belt of the Endocutter Document may be fixed to the cartridge, or movable relative to the cartridge. As another example, where the staple holder 8 is a detachable cartridge, it may hold a number of individual, conventional staples. The staple holder 8 and anvil 6 may be fabricated from any suitable material or materials. As one example, both the staple holder 8 and anvil 6 may be fabricated from stainless steel. As another example, at least one of the staple holder 8 and anvil 6 may be fabricated at least in part from a ceramic material, to provide enhanced stiffness. As another example, the end effector 4 may be any other suitable item for treating or visualizing tissue, such as but not limited to at least one electrode (bipolar or otherwise), adhesive applicator, camera, ultrasound emitter, forceps, or other items. The end effector 4 may be connected to the distal end of a shaft 10. The shaft 10 may be rigid along part or all of its length. Alternately, the shaft 10 may be flexible in whole or in part, or may include an articulating region, such as described in U.S. Pat. No. 7,918,376, issued on Apr. 5, 2011 (the "Articulation Document"), which is hereby incorporated by reference in its entirety.

The handle 12 may be attached to the proximal end of the shaft 10, or any other suitable portion of the shaft 10. The shaft 10 may be fabricated integrally with the handle 12. Alternately, the shaft 10 and the handle 12 may be two separate items that are connected together in any suitable manner. The handle 12 may include any mechanism, mechanisms, structure or structures that are suitably configured to actuate the end effector 4. The handle 12 may be actuated purely by hand, meaning that the handle 12 mechanically converts force applied thereto by hand to force utilized to actuate the end effector 4. As another example, the handle 12 may include a source of stored energy for actuating the end effector 4. The source of stored energy may be mechanical (such as a spring), electrical (such as a battery), pneumatic (such as a cylinder of pressurized gas) or any other suitable source of stored energy. The source of stored energy, its regulation, and its use in actuating the end effector 4 may be as described in commonly-assigned U.S. Pat. No. 7,682,368, issued on Mar. 23, 2010, which is herein incorporated by reference in its entirety. The handle 12 may instead, or also, include a connector or connectors suitable for receiving stored energy from an external source, such as a hose connected to a hospital utility source of pressurized gas or of vacuum, or an electrical cord connectable to a power source.

The handle 12 may include a trigger 14 and a mode button 16. Advantageously, the handle 12 includes a single trigger 14. The single trigger 14 both clamps the end effector 4 and deploys staples from the staple holder 8, as described in greater detail below. The handle 12 may include a palm grip 18 located proximal to the trigger 14. The palm grip 18 and trigger 14 may be configured such that a user can hold the palm grip 18 against his or her hand, and grasp a distal surface of the trigger 14 with one or more fingers of that hand. Alternately, the handle 12 and trigger 14 may be arranged in any other suitable manner. A release button 13 may be included on the handle 12. The release button 13 is actuated to unclamp the end effector 4, as described in greater detail below. A deploy slide 15 may be included on, and slidable relative to, the handle 12. The deploy slide 15 is actuated to reset the surgical stapler 2, as described in greater detail below.

Figure 2:
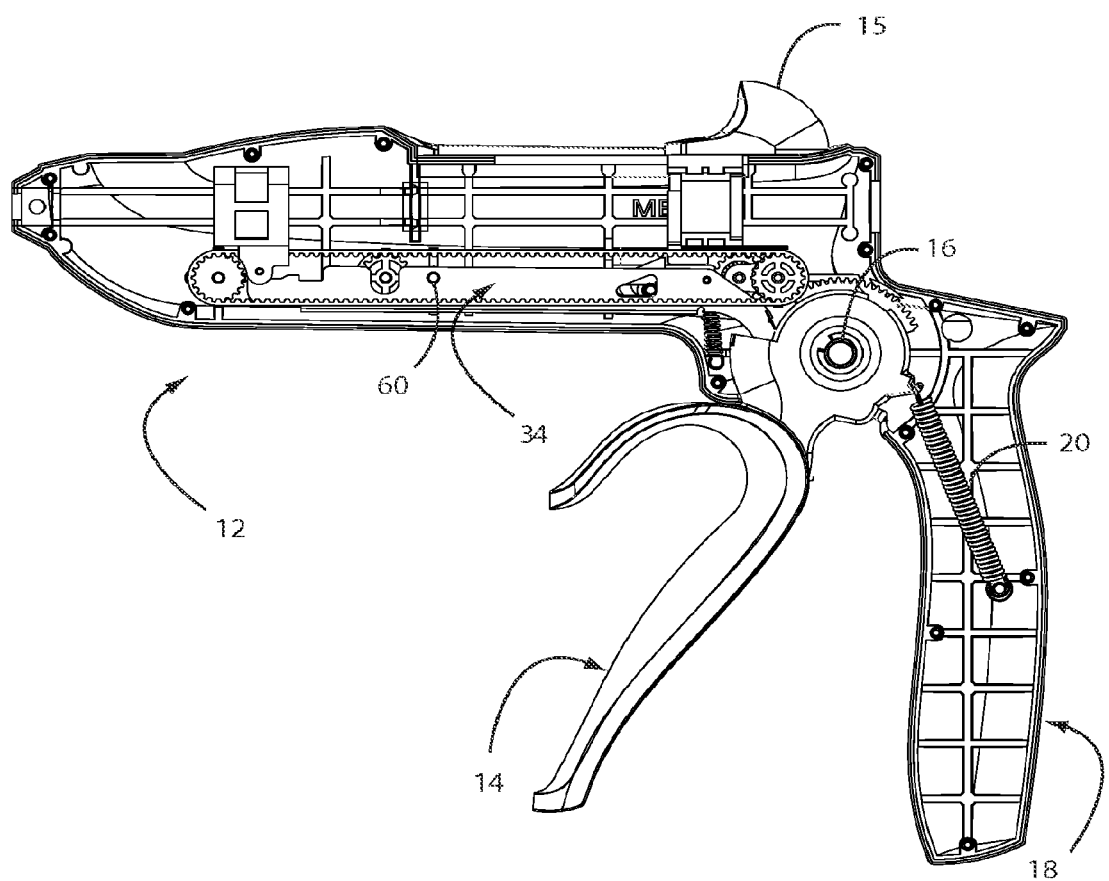
FIG. 2 is a side cutaway view of a handle of the surgical stapler of FIG. 1.
Figure 3:
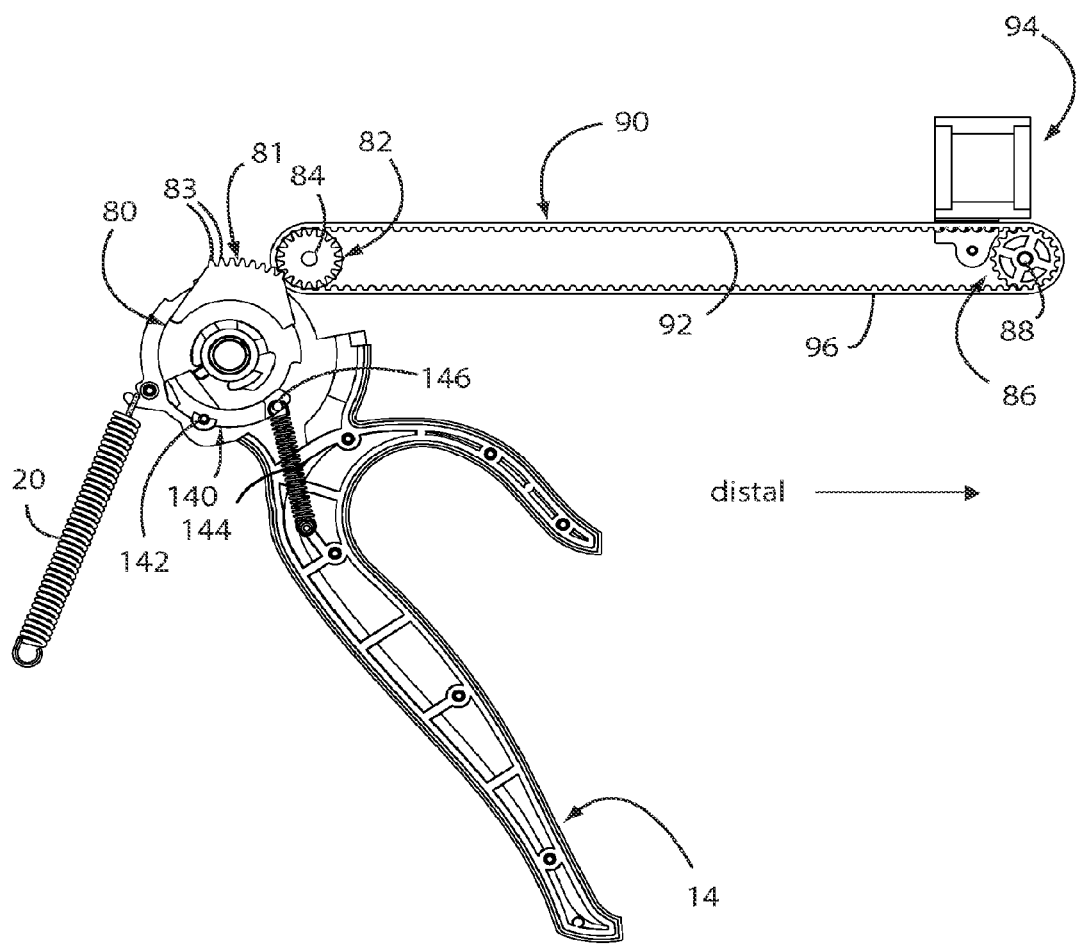
FIG. 3 is a side cutaway view of the handle of the surgical stapler of FIG. 1, from the side opposite to FIG. 2, showing a clamping system in isolation.

Referring also to FIGS. 2-3, the trigger 14 may rotate about the mode button 16. As another example, the trigger 14 may rotate about an axis that is substantially collinear with the axis of the mode button 16. The trigger 14 may be connected to the palm grip 18 by a spring 20 that acts to pull the trigger 14 to a neutral position in which the trigger 14 is spaced apart from the palm grip 18. However, the spring 20 may be omitted if desired. The upper portion of the trigger 14 may be held within the handle 12.

A clamp trigger gear 80 may rotate about the mode button 16 as well. The clamp trigger gear 80 may have an outer perimeter, where an arc 81 of teeth 83 forms part of that outer perimeter of the clamp trigger gear 80. The arc 81 may be an arcuate segment of a circle, and which may be centered on the mode button 16. However, the clamp trigger gear 80 may have a different radius of curvature, shape, and/or different orientation relative to the mode button 16.

The clamp trigger gear 80 selectively engages the clamp belt gear 82, as described in greater detail below. The clamp belt gear 82 may include and be rotatable about an axle 84 that is held by the handle 12. Distal to the clamp belt gear 82, an idler gear 86 may include and be rotatable about an axle 88 that is held by the handle 12. A clamp belt 90 may extend between the clamp belt gear 82 and the idler gear 86. Advantageously, the clamp belt 90 forms a continuous loop, with the gears 82, 86 inside that loop, holding the clamp belt 90 in tension. The clamp belt 90 may include a toothed inner surface 92 that engages the gears 82, 86. Optionally, the teeth on the clamp belt gear 82 that engage the toothed inner surface 92 of the clamp belt 90 may be different from the teeth of the clamp belt gear 82 that engage the clamp trigger gear 80. For example, the teeth on the clamp belt gear 82 that engage the toothed inner surface 92 of the clamp belt 90 may be positioned laterally inward from the teeth of the clamp belt gear 82 that engage the teeth 83 of the clamp trigger gear 80. A clamp slide 94 may be fixed to the clamp belt 90. The clamp slide 94 may be located initially near the distal end of the clamp belt 90, close to or in contact with the idler gear 86. The clamp slide 94 may be fixed to the clamp belt 90 in any suitable manner, and may engage both the inner surface 92 and the outer surface 96 of the clamp belt 90. Alternately, the clamp slide 94 may engage only one surface 92, 96 of the clamp belt 90, or may engage a central portion of the clamp belt 94 between the surfaces 92, 96 rather than engaging the surfaces 92, 96. The clamp slide 94 may have any suitable shape. As one example, referring to FIG. 5, the clamp slide 94 may define a cylindrical passage 98 therein. (Note that the clamp slide 94 is shown in cross-section in FIG. 5.). A clamp slide pin 100, or other structure such as a rod or bar, may be a part of the clamp slide 94, and may extend generally laterally or in any other suitable direction. The clamp slide pin 100 may be positioned under the clamp belt 90. Alternately, the clamp slide pin 100 may be positioned differently. The clamp slide 94 may be fixed to, coupled to, or otherwise engageable with one or more structures or mechanisms that extend from the clamp slide 94 through the shaft 10 to the end effector 4. Clamping of an end effector 4 is described in, for example, commonly-assigned U.S. patent application Ser. No. 12/263,171, filed on Oct. 31, 2008; Ser. No. 12/612,614, filed on Nov. 4, 2009; and Ser. No. 12/840,156, filed on Jul. 20, 2010 (the "Clamping Documents"), all of which are herein incorporated by reference in their entirety.

Figure 4:
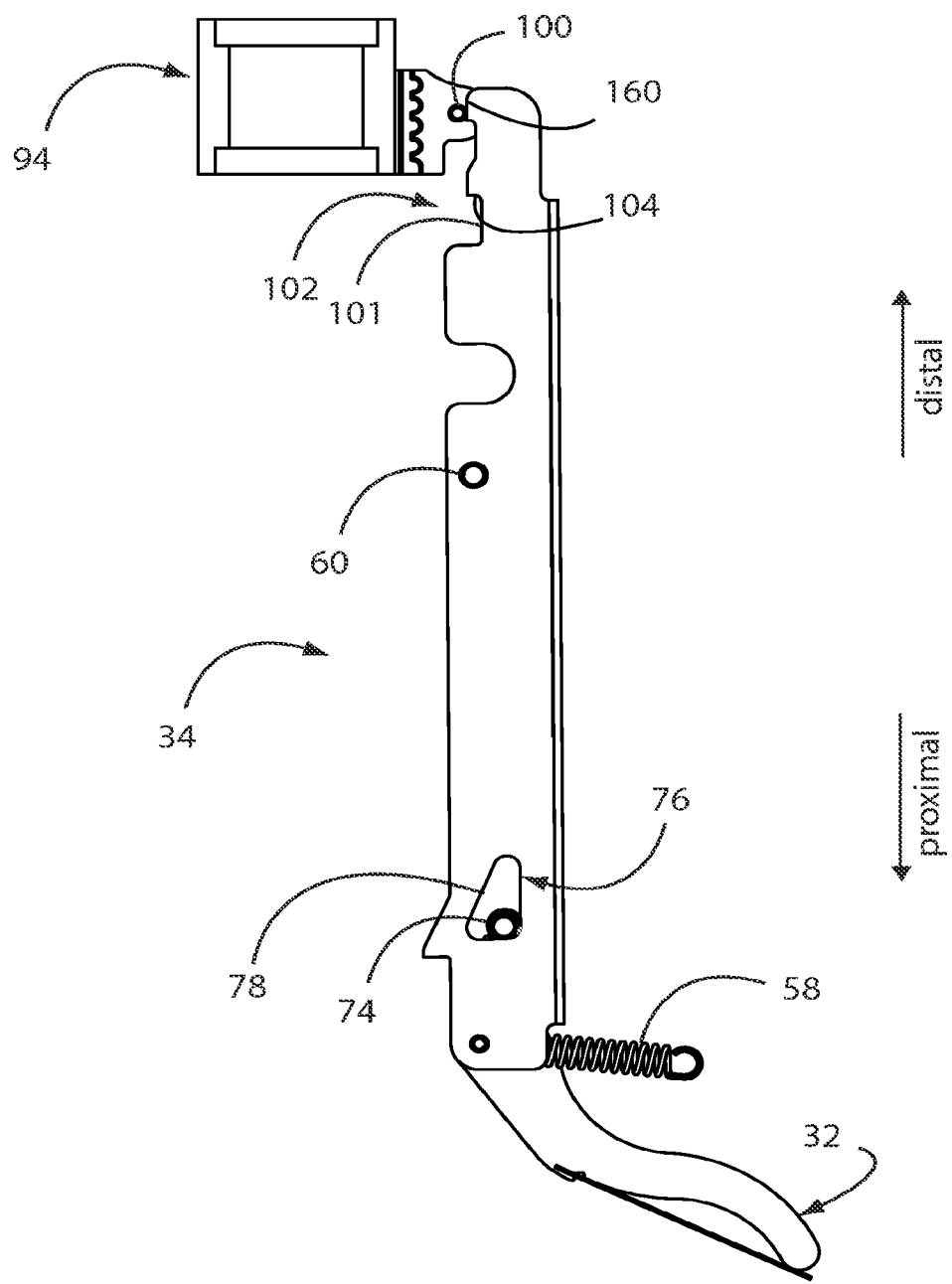
FIG. 4 is a side view of a clamp lock in an unclamped position.
Figure 5:
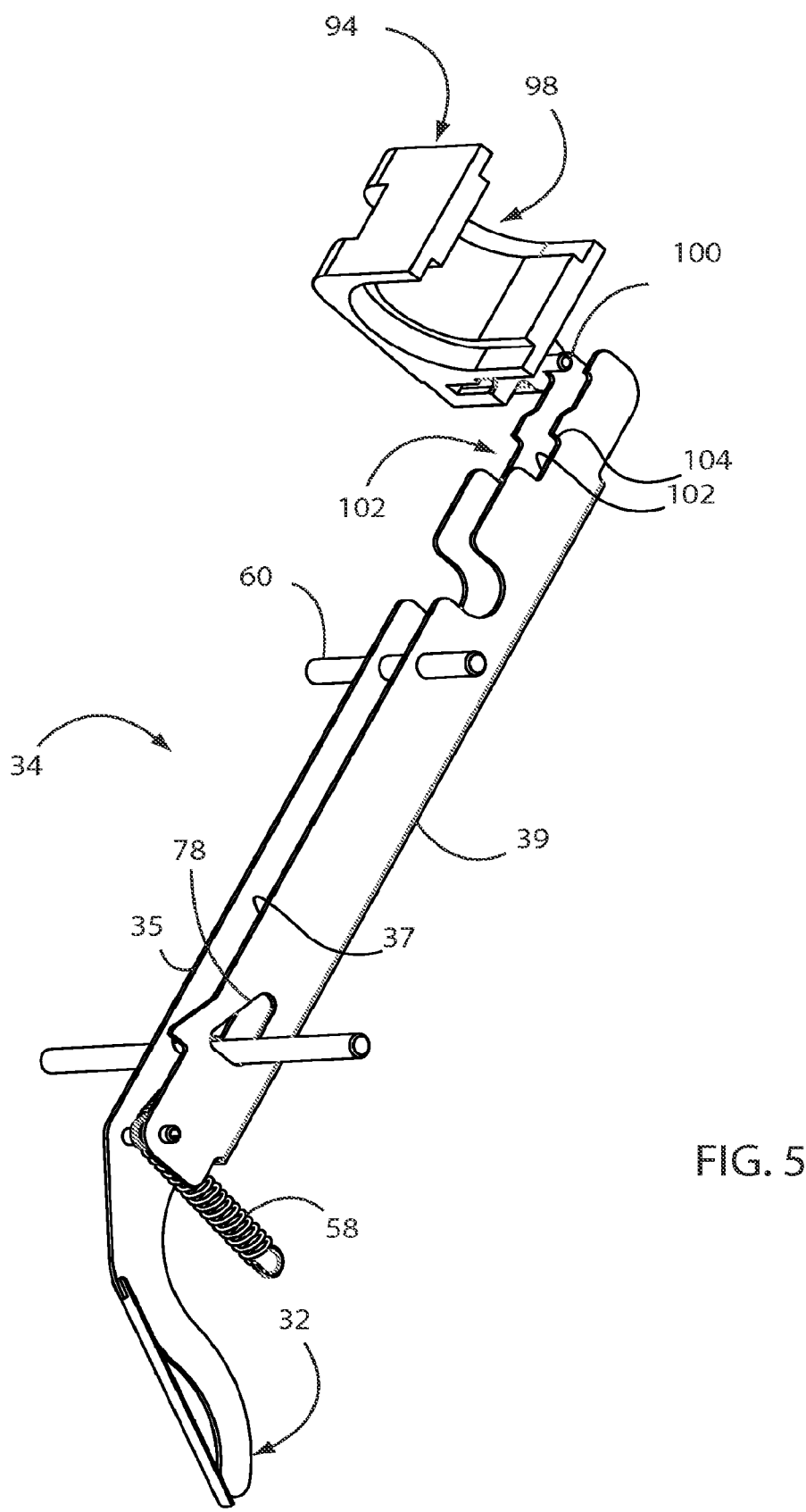
FIG. 5 is a perspective view of the clamp lock of FIG. 4.

Referring also to FIG. 4, a clamp lock 34 is shown. The clamp lock 34 may be generally U-shaped in cross-section, having two lateral walls 35, 37 spaced apart from one another, where those lateral walls 35, 37 may be generally parallel. A lower wall 39 connects the lateral walls 35, 37, and is connected to the lower edge of each lateral wall 35, 37. The lower wall 39 may occupy a plane that is generally perpendicular to the plane of each lateral wall 35, 37. Alternately, the clamp lock 34 may have any other suitable shape and/or cross-section. A pivot pin 60 may extend laterally from at least one side of the clamp lock 34. The pivot pin 60 may be fixed to the clamp lock 34, or may be a pin, rod or similar structure that extends through apertures defined in the clamp lock 34. The pivot pin 60 is held by the handle 12 such that the pivot pin 60 can rotate but not substantially translate. For example, each end of the pivot pin 60 may be held within an open cylindrical structure fabricated as part of, or that is attached to, the handle 12. Alternately, where the pivot pin 60 extends through apertures in the clamp lock 34, the pivot pin 60 may be held completely immobile by the handle 12. A clamp lock tail 32 may extend proximally and downward from the clamp lock 34. The clamp lock tail 32 may have any suitable shape. As one example, as shown in FIGS. 4-5 it may form a gentle S-shape. The clamp lock tail 32 is located proximal to the pivot pin 60. The clamp lock tail 32 may extend from one of the lateral walls 35, 37 of the clamp lock 34, and may be substantially as thick as the lateral wall 35, 37 from which it extends.

A spring 58 may extend from the clamp lock 34 to the handle 12. One end of the spring 58 may be fixed or otherwise attached to the clamp lock 34 at or near the proximal end thereof. Alternately, that end of the spring 58 may be attached to any location on the clamp lock 34 proximal to the pivot pin 60. The other end of the spring 58 may be fixed or otherwise attached to the handle 12. In an initial, preclamped position, the spring 58 is in tension, such that the spring 58 biases the proximal end of the clamp lock 34 downward and the distal end of the clamp lock 34 upward. Alternately, the spring 58 may be located distal to the pivot pin 60 and fixed to the handle 12 in such a way that in an initial, preclamped position, the spring 58 biases the proximal end of the clamp lock 34 downward and the distal end of the clamp lock 34 upward.

Figure 6:
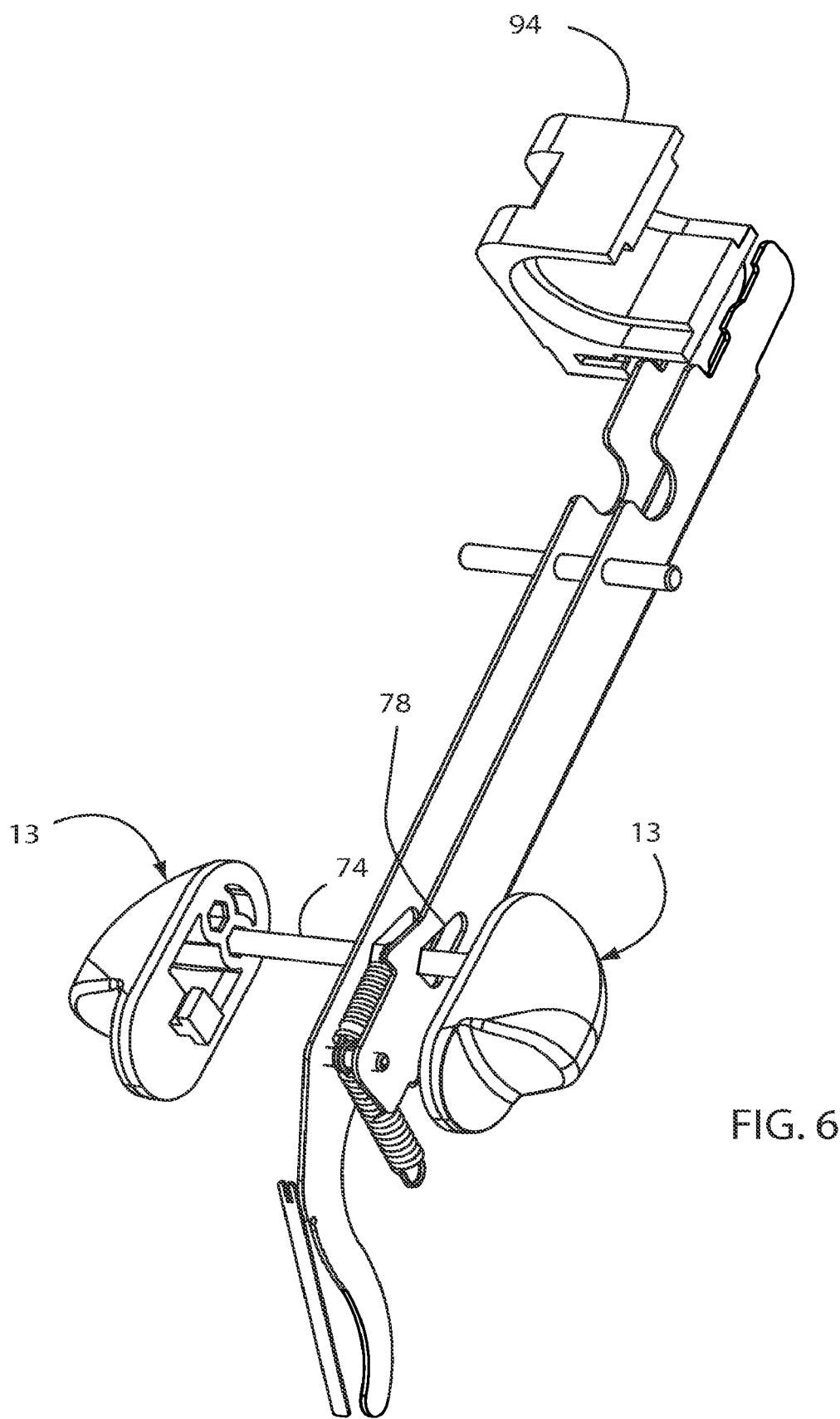
FIG. 6 is a perspective view of the clamp lock of FIG. 4, including the unclamp rod and release buttons.

A detent 102 may be defined in at least one lateral wall 35, 37 of the clamp lock 34, distal to the pivot pin 60. The detent 102 acts to hold the clamp slide pin 100 in place when the end effector 4 is clamped, as described in greater detail below. When the end effector 4 is clamped, the clamp slide pin 100 is located at a longitudinal position that is more proximal than the position of the clamp slide pin 100 when the end effector 4 is unclamped, and interference between the clamp slide pin 100 and the front wall 104 of the detent 102 holds the surgical stapler 2 in that clamped configuration. An unclamp aperture 76 may be defined through at least one lateral wall 35, 37 of the clamp lock 34. The unclamp aperture 76 may have any suitable shape. As one example, the unclamp aperture 76 may be generally triangular, with an upper surface 78 that slopes downward in the distal direction. An unclamp rod 74 may extend through each unclamp aperture 76, and may be fixed or otherwise connected to at least one release button 13. As seen in FIG. 6, two release buttons 13 may be provided, one on each lateral side of the handle 12, with the unclamp rod 74 extending between the two release buttons 13. As seen in FIGS. 4-5, the unclamp rod 74 and the clamp lock 34 are in an unclamped position, and as seen in FIG. 6, the unclamp rod 74 and the clamp lock 34 are in a clamped position.

Figure 7:
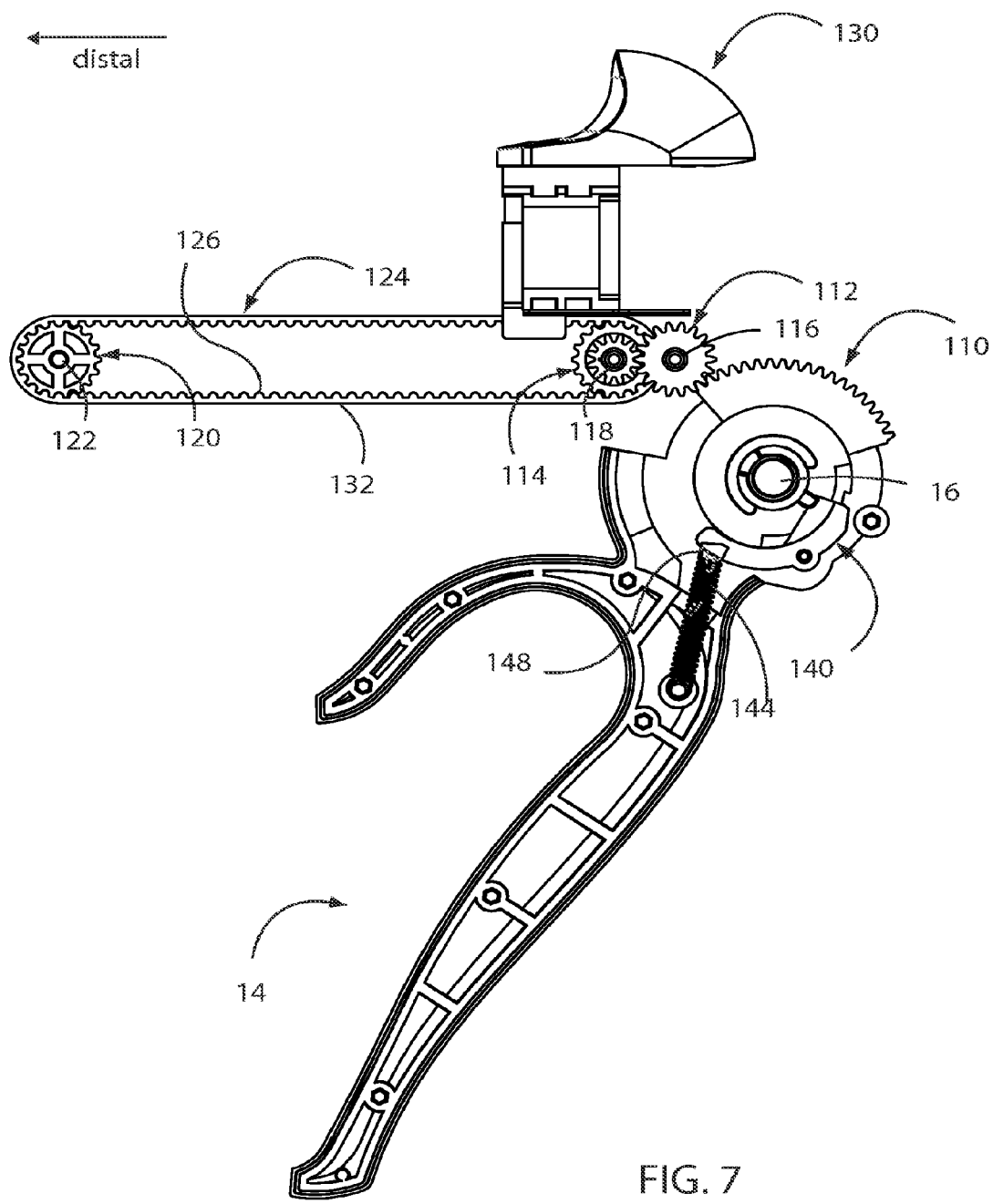
FIG. 7 is a side cutaway view of the handle of the surgical stapler of FIG. 1, from the same side as FIG. 2, showing a deployment system in isolation.
Figure 8:
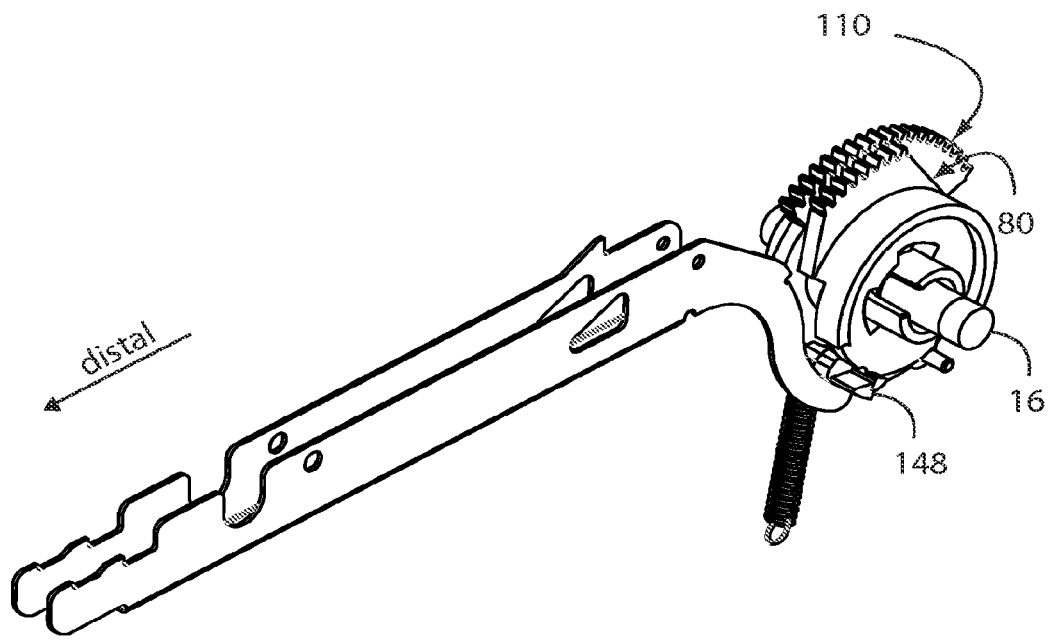
FIG. 8 is a perspective cutaway view of the handle of the surgical stapler of FIG. 1, from the same side as FIG. 2, showing a mode switching system in isolation.

Referring also to FIG. 7, a deployment trigger gear 110 may rotate about the mode button 16 as well. The deployment trigger gear 110 may have an outer perimeter, where an arc 53 of teeth 55 forms part of the perimeter of the deployment trigger gear 110. The arc 53 may be an arcuate segment of a circle, and which may be centered on the mode button 16. However, the deployment trigger gear 110 may have a different radius of curvature, shape, and/or different orientation relative to the mode button 16. Referring also to FIG. 8, the deployment trigger gear 110 may be substantially parallel to and laterally spaced apart from the clamp trigger gear 80. The clamp trigger gear 80 may be on the left, looking along the handle 12 in the distal direction, and the deployment trigger gear 110 may be on the right. However, the lateral positions of the gears 80, 110 may be reversed if desired. As another example, the clamp trigger gear 80 and the deployment trigger gear 110 need not be spaced apart, and may be laterally in contact with one another.

The arc 53 of teeth 55 of the deployment trigger gear 110 selectively engages the reversing gear 112, as described in greater detail below. The reversing gear 112 advantageously engages the deployment belt gear 114 at all times. The purpose of the reversing gear 112 is to convert the forward rotational motion of the deployment trigger gear 110 into rotation of the deployment belt gear 114 in the same direction. The reversing gear 112 may include and be rotatable about an axle 116 that is held by the handle 12. The deployment belt gear 114 may include and be rotatable about an axle 118 that is held by the handle 12. Distal to the deployment belt gear 114, an idler gear 120 may include and be rotatable about an axle 122 that is held by the handle 12. A deployment belt 124 may extend between the deployment belt gear 114 and the idler gear 120. Advantageously, the deployment belt 124 forms a continuous loop, with the gears 114, 120 inside that loop, holding the deployment belt 124 in tension. The deployment belt 124 may include a toothed inner surface 126 that engages the gears 114, 120. Optionally, the teeth on the deployment belt gear 114 that engage the toothed inner surface 126 of the deployment belt 124 may be different from the teeth that engage the reversing gear 112. For example, the teeth on the deployment belt gear 114 that engage the toothed inner surface 126 of the deployment belt 124 may be positioned laterally inward from the teeth of the deployment belt gear 114 that engage the reversing gear 112. A deployment slide 130 may be fixed to the deployment belt 124. The clamp slide 94 may be located initially near the proximal end of the deployment belt 124, close to or in contact with the deployment belt gear 114. The deployment slide 130 may be fixed to the deployment belt 124 in any suitable manner, and may engage both the inner surface 126 and the outer surface 132 of the deployment belt 124. Alternately, the deployment slide 130 may engage only one surface 126, 132 of the deployment belt 124, or may engage a central portion of the deployment belt 124 between the surfaces 126, 132 rather than engaging the surfaces 126, 132. The deployment slide 130 may have any suitable shape.

Figure 9:
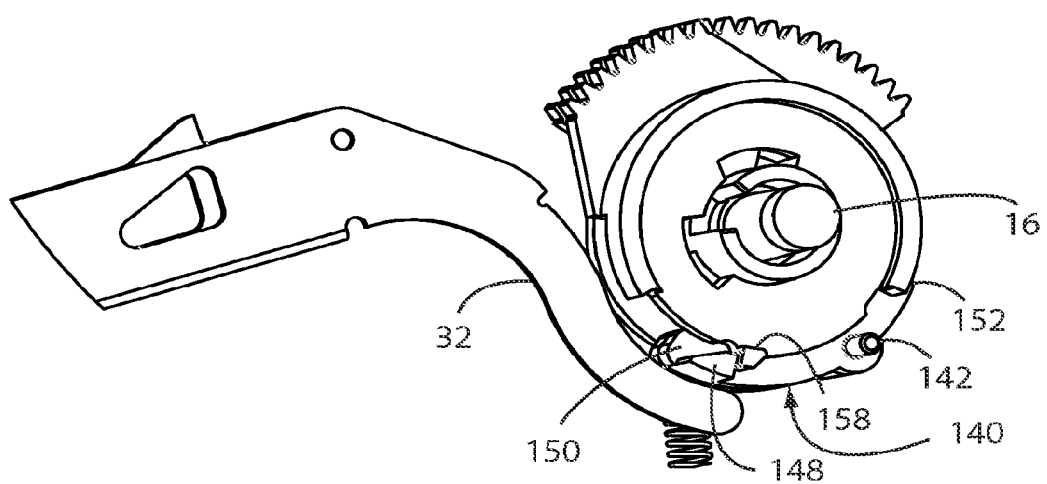
FIG. 9 is a different perspective view of the mode switching system in isolation of FIG. 8, in an initial position.

Referring also to FIGS. 3 and 7, a ratchet 140 engages both the clamp trigger gear 80 and the deployment trigger gear 110. Referring also to FIGS. 8-9, the ratchet 140 is pivotable about the ratchet pivot 142, which is a pin or other structure held by the trigger 14 and about which the ratchet 140 can rotate. The ratchet pivot 142 may be fixed to the ratchet 140, in which case the ratchet pivot 142 is held by but rotatable relative to the handle 12. As another example, the ratchet pivot 142 may be fixed to the handle 12, rotationally as well as translationally, in which case the ratchet pivot 142 may extend through an aperture in the ratchet 140 such that the ratchet can pivot about the fixed ratchet pivot 142. A ratchet spring 144 may be fixed or otherwise connected to the ratchet 140, at a location distal to the ratchet pivot 142. The ratchet spring 114 may be connected to a pin 146 or other feature extending from a remainder of the ratchet 140, or may be connected directly to the ratchet 140 itself. Thus, in an initial configuration, the distal end 150 of the ratchet 140 is biased downward as a consequence of tension in the ratchet spring 144, and the proximal end 152 of the ratchet 140 (proximal to the ratchet pivot 142) is biased upward as a consequence of the freedom of the ratchet 140 to rotate about the ratchet pivot 142. At least one ratchet tooth 148 may extend laterally from the ratchet 140. As shown in FIGS. 8-9, the ratchet tooth 148 may extend laterally in the leftward direction, as viewed from the proximal toward the distal direction. The ratchet tooth 148 may be shaped as a triangular solid, or may have any other suitable shape. A clamp trigger gear tooth 158 may similarly extend laterally from the clamp trigger gear 80.

Figure 10:
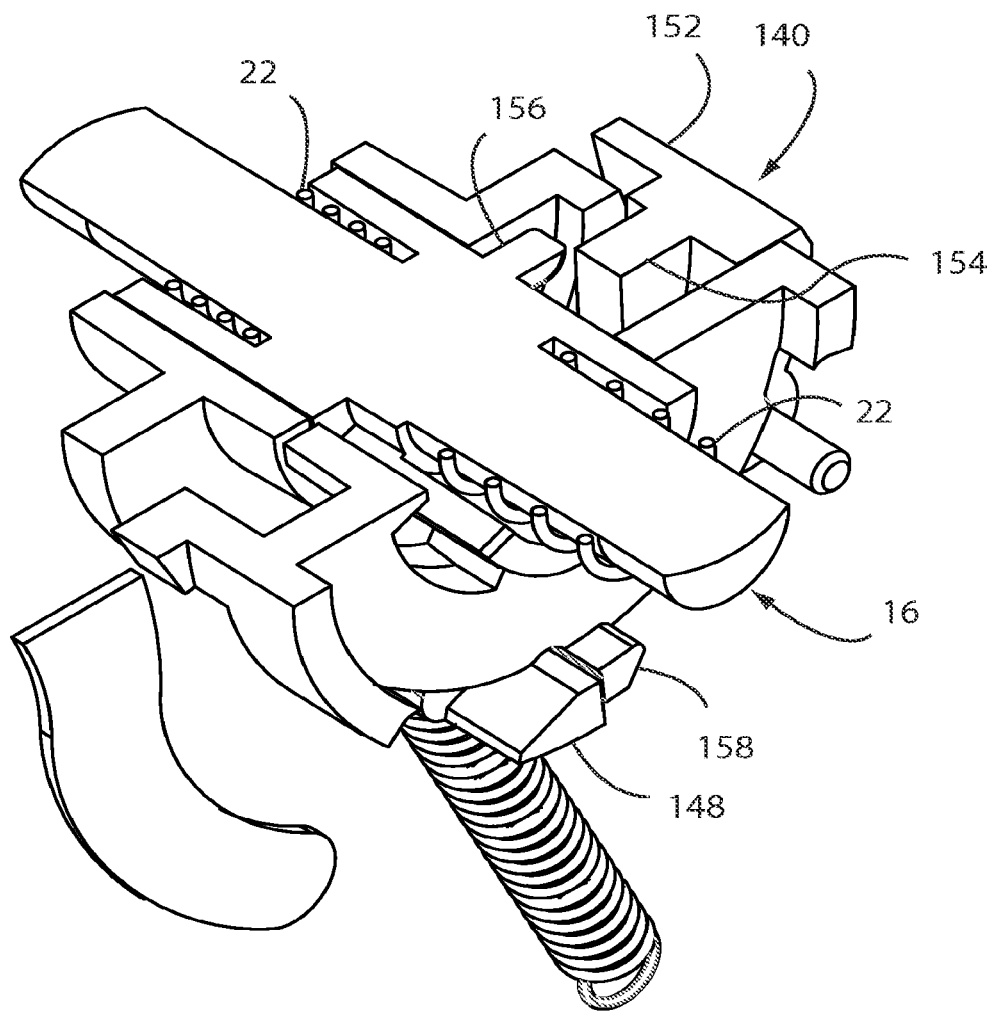
FIG. 10 is a perspective cross-section view of a mode switch in an initial, neutral position.
Figure 11:
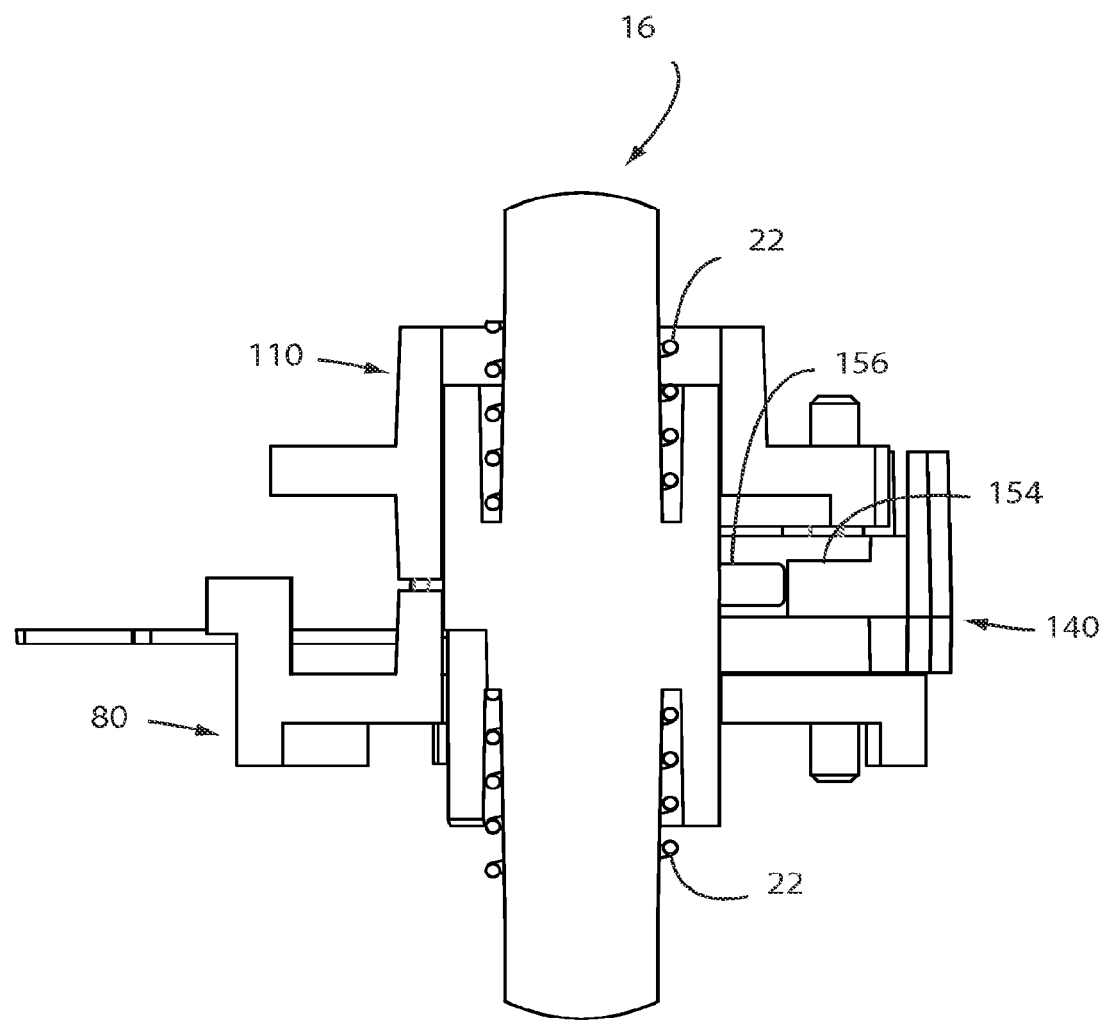
FIG. 11 is a top cross-section view of FIG. 10.

Referring also to FIGS. 10-11, a ratchet rib 150 may extend inward from the proximal end 152 of the ratchet 140 or a location in proximity to the proximal end 152 of the ratchet 140. As another example, the ratchet rib 150 may extend inward from a different part of the ratchet. In the initial neutral position and in the clamped position, as shown in FIG. 10, the ratchet rib 150 engages a mode switch post 156 that extends outward from the mode switch 16. At least one spring 22 may wrap around the mode button 16 to bias the mode button 16 to the neutral position shown in FIG. 3. Advantageously, two springs 22 are utilized, one on either lateral side of the mode button 16. The lateral outward end of each spring 22 may press against an interior surface of the handle 12 or other structure or mechanism within the handle 12 in order to bias the mode button 16 to the neutral position.

Operation: Clamping

Initially, the surgical stapler 2 is in a neutral, unclamped configuration. In the unclamped configuration, the distal end of the anvil 6 is spaced apart from the distal end of the staple holder 8, such that the end effector 4 may be moved relative to tissue in order that the end effector 4 holds tissue between the anvil 6 and the staple holder 8. The user possesses the surgical stapler 2 in hand, grasping the handle 12, and places the end effector 4 as that user sees fit, whether during an open surgical procedure, or a minimally-invasive surgical procedure performed through a port in the body such as a trocar port or through a natural orifice in the body. The surgical stapler 2 instead, or also, may be used in conjunction with or by a surgical robot (such as the Da Vinci™ surgical robot of Intuitive Surgical of Sunnyvale, Calif.).

Referring to FIGS. 4 and 8-9, in the initial, unclamped configuration, the clamp lock tail 32 is positioned underneath the ratchet tooth 148 and in contact with the ratchet tooth 148. The clamp lock 34 may be oriented substantially horizontally within the handle 12 in the initial, unclamped position. Even though the spring 58 biases the proximal end of the clamp lock 34 downward, it is not biased so far downward that the clamp lock tail 32 is moved out of engagement with the ratchet tooth 148. Engagement between the clamp lock tail 32 and the ratchet tooth 148 lifts the ratchet tooth 148 upward in the initial, unclamped configuration. Consequently, the distal end 150 of the ratchet 150 is pivoted upward about the ratchet pivot 142, and the proximal end 152 of the ratchet 150 is pivoted downward about the ratchet pivot 142. In this position, the proximal end 152 of the ratchet 150 is spaced apart from the deployment trigger gear 110. That is, the proximal end 152 of the ratchet 150 "stands off" from the deployment trigger gear 110. In this way, the ratchet 150 is disengaged from the deployment trigger gear 110 in the initial, unclamped configuration. Further, referring also to FIG. 10, the ratchet rib 154 may contact the mode switch post 156 in the initial, unclamped configuration of the surgical stapler 2. Such contact between the ratchet rib 154 and mode switch post 156 also may cause the proximal end 152 of the ratchet 150 to stand off from the deployment trigger gear 110. The ratchet tooth 148 is located distal to, and in contact with, the clamp trigger gear tooth 158.

When the user is ready to clamp tissue between the anvil 6 and staple holder 8, the user squeezes the trigger 14 toward the palm grip 18. Referring to FIGS. 3 and 8-9, this motion causes the trigger 14 to rotate about the mode button 16. The ratchet pivot 142 is fixed relative to the trigger 14, such that rotation of the trigger 14 causes the ratchet pivot 142, and the ratchet 140 itself, to rotate as well. Such rotation causes the ratchet tooth 148 to exert a force on the clamp trigger gear tooth 158, which in turn causes the clamp trigger gear 80 to rotate as well. This rotation causes the teeth 83 of the clamp trigger gear 80 to rotate proximally. The clamp trigger gear 80 engages the clamp belt gear 82, such that rotation of the teeth 83 causes a counterrotation of the clamp belt gear 82. Engagement between the clamp belt gear 82 and the clamp belt 90, such as by engagement between teeth of the clamp belt gear 82 and a toothed inner surface 92 of the clamp belt gear 82, causes the clamp belt 90 to move. The upper portion of the clamp belt 90 may move proximally, and the lower portion of the clamp belt 90 may move distally.

This motion of the clamp belt 90 may cause the clamp slide 94, which may be fixed to the upper portion of the clamp belt 90, to move proximally. Referring to FIG. 4, initially the clamp slide pin 100, which may be fixed to the clamp slide 94, is located against a first surface 160 of the clamp lock 34. That first surface 160 may be located on the upper surface of at least one of the walls 35, 37 of the clamp lock 34, and may be located near the distal end of that wall or those walls 35, 37. The first surface 160 is biased into contact with the clamp slide pin 100 as a result of tension applied to the proximal end of the clamp lock 34 by the spring 58. That spring 58 urges the proximal end of the clamp lock 34 downward, and due to the pivot pin 60 located distal to the spring 58, the spring 58 also urges the distal end of the clamp lock 34 upward. The first surface 160 may be flat, curved, angled or complex; as seen in FIG. 4, for example, the first surface 160 may be generally flat at its distal end, angle upward toward the proximal direction, and then include another flat segment. As the clamp slide pin 100 moves proximally as a result of proximal motion of the upper portion of the clamp belt 90, the clamp slide pin 100 moves proximal to the first surface 160, to the detent 102. The clamp slide pin 100 does not change its vertical position in the handle 12. However, the spring 58 continues to bias the distal end of the clamp lock 34 upward. Thus, when the clamp slide pin 100 moves proximally to the detent 102, the distal end of the clamp lock 34 rotates upward such that the clamp slide pin 100 is now located within the detent 102, against the lower surface 101 of the detent 102. The presence of the clamp slide pin 100 in the detent 102 locks the clamp slide pin 100 within the detent 102, and thus holds the clamp slide 94 in place longitudinally. Further, as the clamp lock 34 rotates, the unclamp aperture 76 rotates such that the unclamp rod 74 is located against an upper surface of that unclamp aperture 76.

Where the unclamp aperture 76 is triangular and includes an upper surface 78 that angles downward in the distal direction, the unclamp rod 74 may then occupy a position at an upper corner of the unclamp aperture 76, at the proximal end of the upper surface 78.

As set forth in the Clamping Documents, the clamp slide 94 may be fixed to or otherwise connected to a mechanism or mechanisms that extend through the shaft 10 to the end effector 4, such that proximal motion of the clamp slide 94 causes clamping of the end effector 4. "Clamping" refers to relative motion of the anvil 6 and staple holder 8 toward one another, with tissue held between the anvil 6 and staple holder 8.

Operation: Staple Deployment

If the user is satisfied with tissue clamping, then the user may proceed to deploy staples. To change to staple deployment mode, the user may depress the mode button 16 laterally. The mode button 16 may be pressed from left to right or from right to left. For convenience in description, the switch from clamping mode to staple deployment mode is described as occurring in response to a depression of the mode button from left to right. The directions "left" and "right" are determined looking distally along the handle 12.

As the mode button 16 moves laterally, the mode switch post 156 that extends outward from the mode switch 16 also moves laterally. As the mode switch post 156 slides to the right, it moves out of engagement with the ratchet rib 154, such that contact between the mode switch post 156 and the ratchet rib 154 no longer holds off the proximal end 152 of the ratchet 140 from the deployment trigger gear 110. Further, the clamp lock tail 32 has moved out of engagement with the ratchet tooth 148 and stands off from the ratchet tool 148, as a result of the rotation of the clamp lock 34 due to motion of the clamp slide pin into the detent 102. Consequently, the proximal end 152 of the ratchet 140 is no longer held off from the deployment trigger gear 110, and rotates about the mode button 16 to engage the deployment trigger gear 110.

Figure 12:
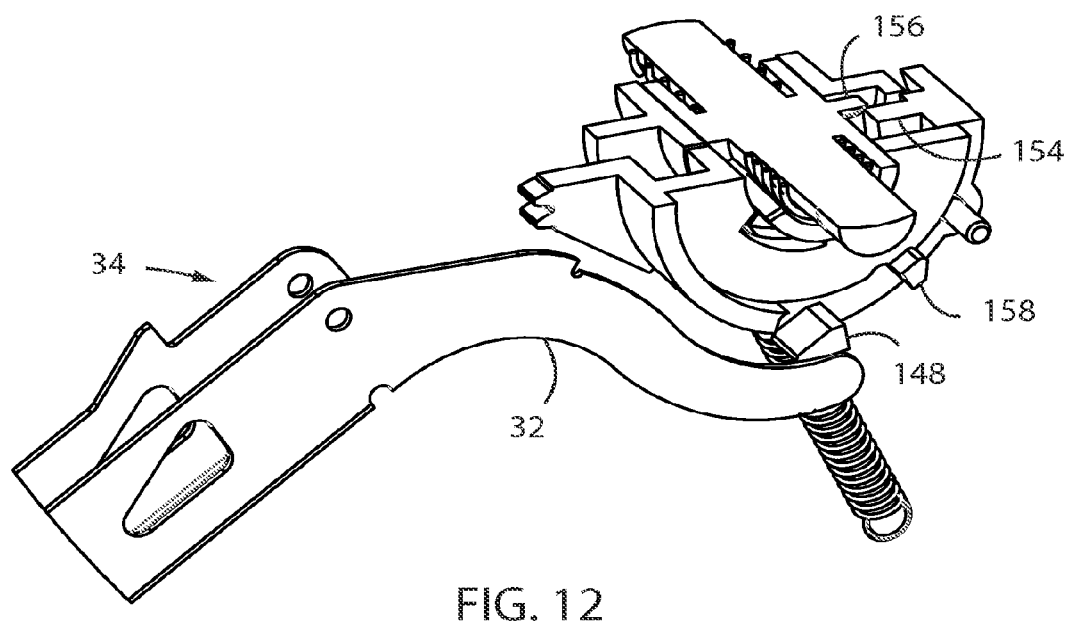
FIG. 12 is a perspective view of the mode switch of FIG. 10 and part of the clamp lock of FIG. 4 in a clamped position.
Figure 13:
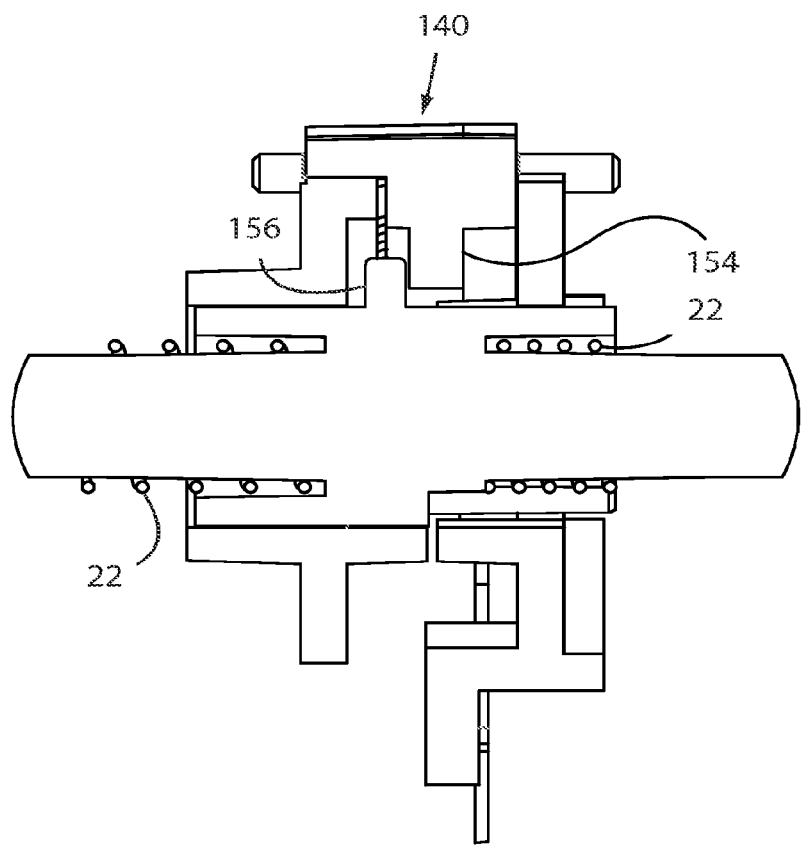
FIG. 13 is a top cross-section view of FIG. 10 in a deployment position.
Figure 14:
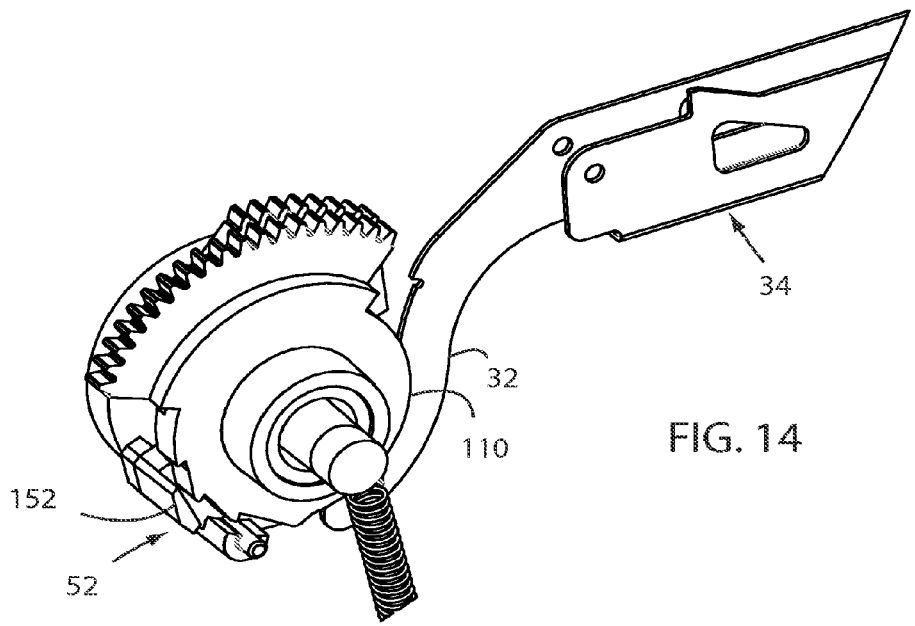
FIG. 14 is a different perspective view of the mode switching system in isolation of FIG. 9, in an initial position.
Figure 15:
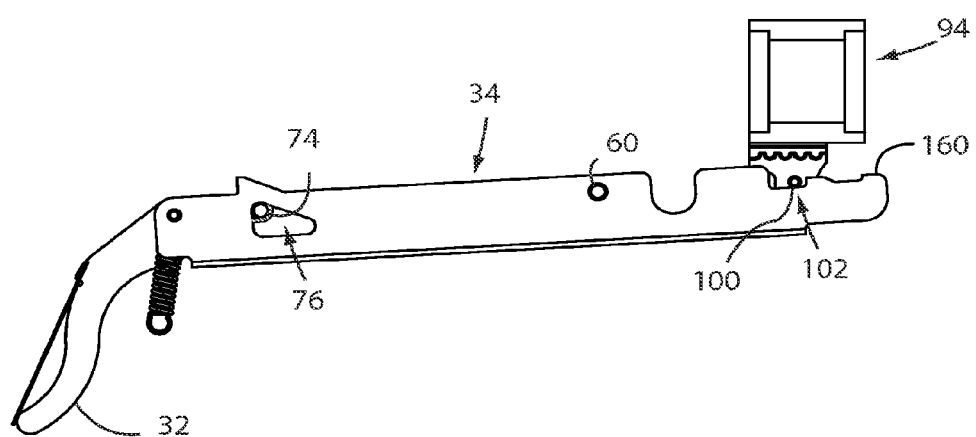
FIG. 15 is a side view of the clamp lock of FIG. 4 in a clamped position.

The user may then release the trigger 14. The trigger 14 returns toward its initial position. Referring also to FIG. 15, the clamp slide pin 100 is held within the detent 102. Where the clamp slide 94 is biased proximally, the clamp slide pin 100 may be located at the distal end of the detent 102. The detent 102 holds the clamp slide pin 100 in place, which in turn holds the clamp belt 90 in place, which in turn prevents rotation of the clamp belt gear 82, which in turn prevents rotation of the clamp trigger gear 80. Thus, referring also to FIG. 12, as the trigger 14 rotates about the mode button 16 toward its initial position, and as the ratchet pivot 142 rotates with the trigger 14, the clamp trigger gear 80 is held stationary in place in a clamped position. In that clamped position, the clamp trigger gear tooth 158 is stationary as well, and the ratchet tooth 148 rotates to a position arcuately spaced apart from the clamp trigger gear 158.

Figure 16:
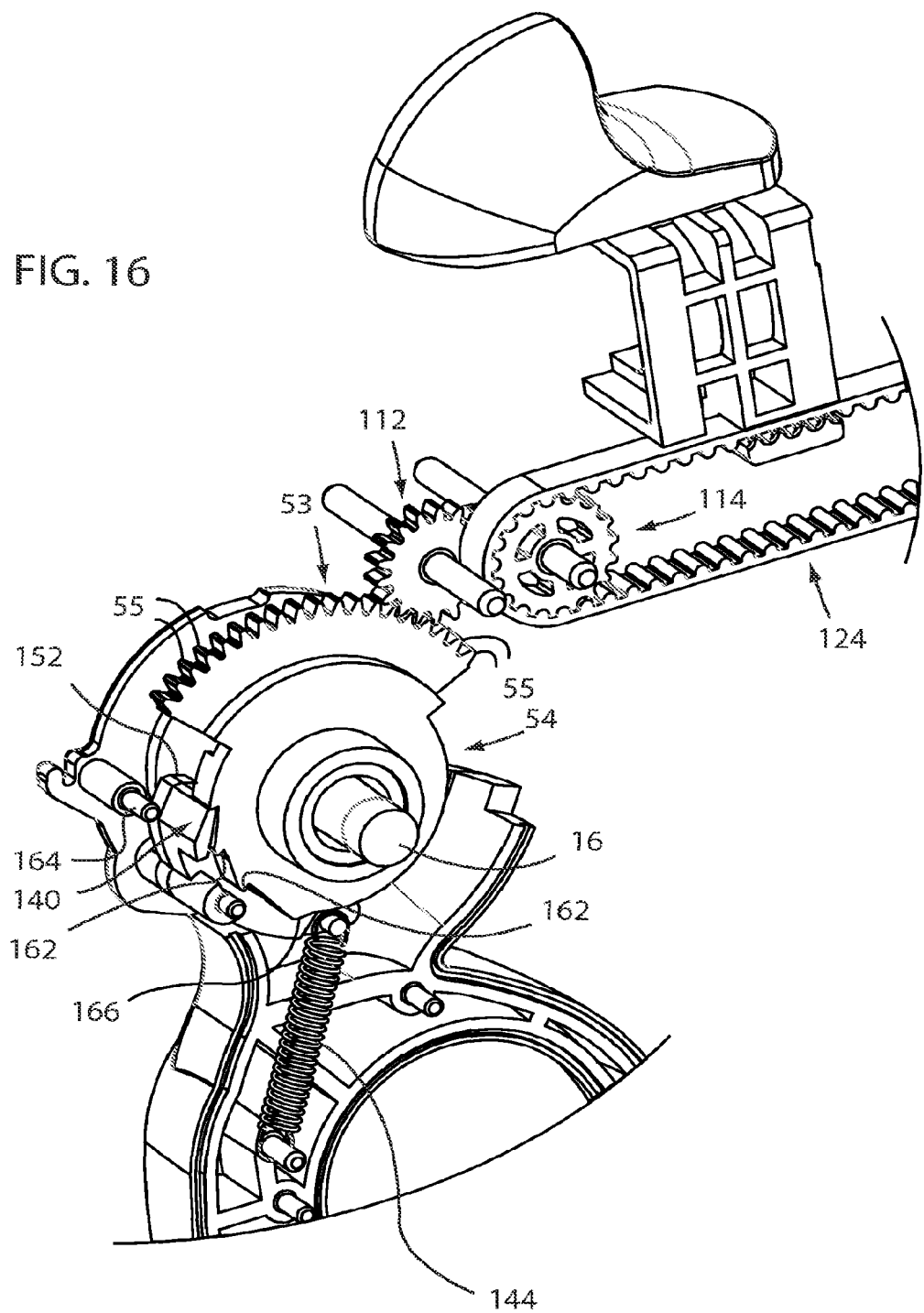
FIG. 16 is a perspective view of the deployment system of FIG. 7 in deployment mode, before firing staples.
Figure 17:
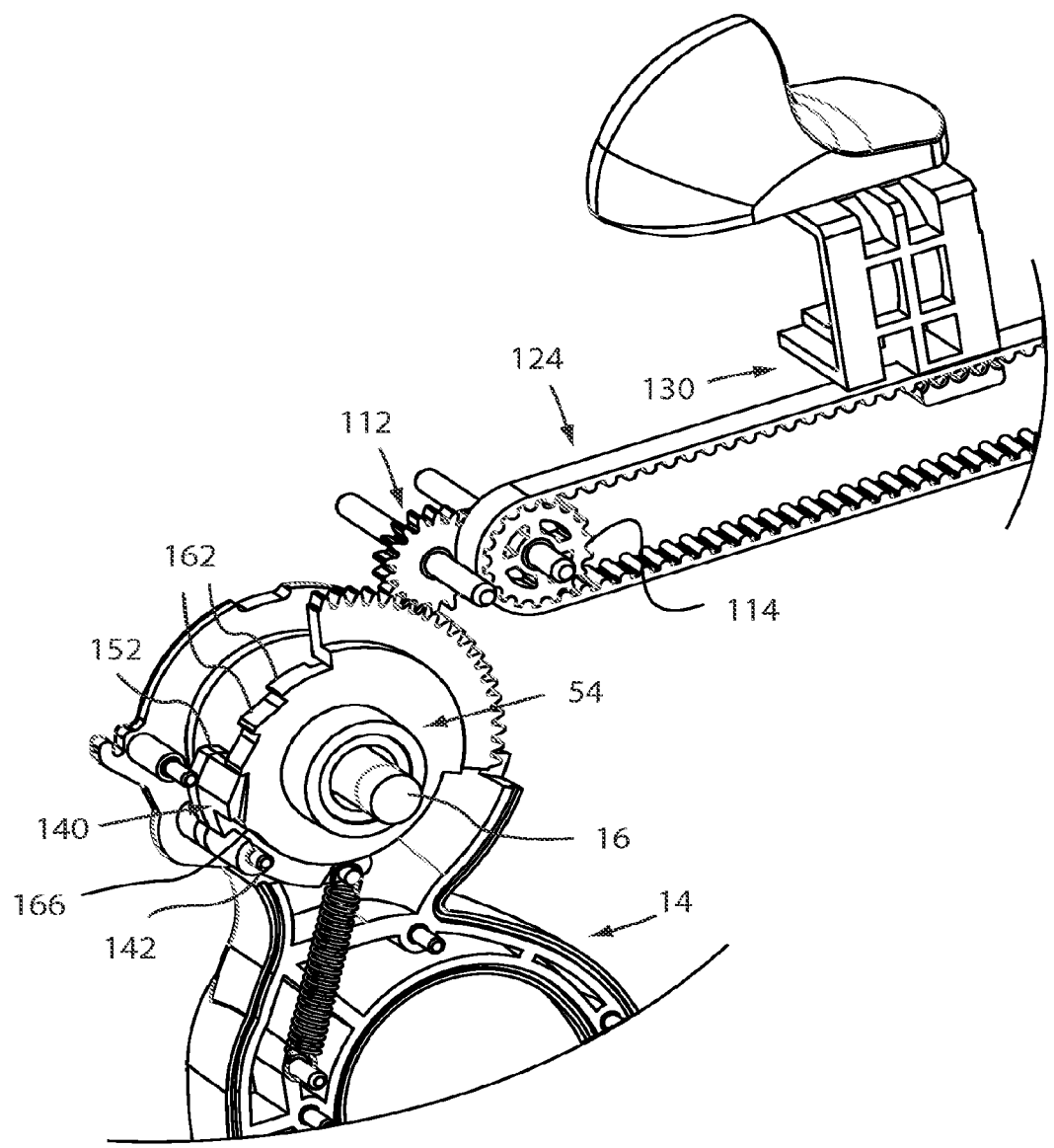
FIG. 17 is the perspective view of FIG. 16, after firing staples.

The trigger 14 is now disengaged from the clamp trigger gear 80 and engaged with the deployment trigger gear 110, as seen in FIG. 16. The deployment trigger gear 110 may include outer teeth 162 along at least part of an outer perimeter thereof. The ratchet 140 may be engaged with the deployment trigger gear 110 such that the proximal end 152 of the ratchet 140 abuts one of the outer teeth 162 of the deployment trigger gear 110.

The user may then depress the trigger 14 toward the palm grip 18. The trigger 14 rotates about the mode button 16, and as set forth above, rotation of the trigger 14 causes the ratchet pivot 142 to rotate about the mode button 16. As the trigger 14 and ratchet 140 rotate, the proximal end 152 of the ratchet 140 imparts a force to the abutting outer tooth 162, causing the deployment trigger gear 110 to rotate about the mode button 16 as well. As the deployment trigger gear 110 rotates, the arc 53 of teeth 55 that form part of the perimeter of the deployment trigger gear 110 rotates as well. The arc 53 describes an arcuate angle centered on the mode button 16 that is equal to or less than the arcuate angle centered on the mode button between the ratchet tooth 148 and the clamp trigger gear tooth 158. As the arc 53 rotates, the teeth 55 that engage the reversing gear 112 cause the reversing gear 112 to rotate in the reverse direction. Engagement between the reversing gear 112 and the deployment belt gear 114 causes the deployment belt gear 114 to rotate in the same direction as the trigger 14. Engagement between the deployment belt gear 114 and the deployment belt 124, such as by engagement between teeth of the deployment belt gear 114 and a toothed inner surface 126 of the deployment belt gear 114, causes the deployment belt 124 to move. The upper portion of the clamp belt 90 may move distally, and the lower portion of the clamp belt 90 may move proximally.

This motion of the deployment belt 124 may cause the deployment slide 130, which may be fixed to the upper portion of the deployment belt 124, to move distally. Motion of the deployment slide 130 may result in distal motion of a wire or other structure that extends through the shaft 10 to the staple holder 8 and that may cause one or more wedges to sequentially deform and shear staples from a feeder belt, as set forth in the Endocutter Document. The arc 53 may define an angle that, when the trigger 14 is rotated through that angle, less than all of the staples are deployed. For example, three actuations of the trigger 12 may be required in order to fire all of the staples from the staple holder 8. If so, the location of the deployment slide 130 on the handle 12 provides an indicator to the user of how many actuations have been performed and how many remain before completion of staple deployment. After the trigger 14 has been rotated through the arc 53, the trigger return spring 164 urges the trigger 14 back toward its initial position. The ratchet pivot 142 rotates with the trigger 14, causing the ratchet 140 to rotate relative to the deployment trigger gear 110, which remains stationary. As the trigger 14 rotates back to its initial rotational position, the ratchet 140 slides over the surface of the outer teeth 162 without engaging them or rotating the deployment trigger gear 110, because the outer teeth 162 are shaped to only engage the ratchet 140 in one rotational direction. The ratchet 140, being a ratchet, operates to engage and rotate the deployment trigger gear 110 in only one rotational direction. Alternately, the ratchet 140 may be held off from the deployment trigger gear 110 as the trigger 14 returns to its original position. As the ratchet 140 pivots about the mode button 16, the proximal end 152 of the ratchet 140 slides over the next outer tooth 162 in sequence, then snaps down behind that outer tooth 162.

The trigger 14 is then actuated again as described above. Where the trigger 14 is actuated three times in order to deploy all of the staples from the staple holder 8, the trigger 14 is actuated one more time, for a total of three actuations. Referring to FIG. 15, at the end of the third actuation, the trigger 14 has returned to the neutral position, and the proximal end 152 of the ratchet 140 is located behind the last of three outer teeth 162 in the deployment trigger gear 110.

Operation: Unclamping and Resetting

In order to unclamp the end effector 4, the trigger 14 is actuated one final time. As the deployment trigger gear 110 rotates once again about the mode button 16, an unclamp cam 166 moves into contact with the proximal end 152 of the ratchet 140. The unclamp cam 166 is located radially further away from the mode button 16 than the most-outward surface of each of the outer teeth 162. Referring also to FIG. 10, as the proximal end 152 of the ratchet 140 encounters the unclamp cam 166, the proximal end 152 of the ratchet 140 is rotated about the ratchet pivot 142. This rotates the proximal end 152 of the ratchet 140 far enough away from the mode button 16 such that the ratchet rib 154 moves radially outward from the mode switch post 156. Consequently, absent lateral interference between the ratchet rib 154 and the mode switch post 156, the springs 22 urge the mode button 16 toward its initial, neutral lateral position. The mode switch post 156 once again holds the ratchet rib 154 outward. Thus, as the deployment trigger gear 110 continues its rotation, past the unclamp cam 166, the ratchet rib 154 is held off the deployment trigger gear 110, as in the initial state, and deployment is complete.

Optionally, the surgical stapler 2 may now be reset. The reset step may be omitted where the surgical stapler 2 is a single-use device (such as a cartridge-based device), or where the surgical stapler 2 is capable of multiple actuations but only a single group of staples was applied by the user. To reset the surgical stapler 2, the user pulls the deployment slide 130—which is now at its most distal position—proximally. Because the deployment slide 130 is fixed to the deployment belt 124, this motion of the deployment slide 130 causes the deployment belt 124 to move in the opposite direction as during deployment of the staples, such that the upper portion of the deployment belt 124 moves proximally. This motion of the deployment belt 124 causes the deployment belt gear 114 and the reversing gear 112 to rotate in the opposite direction as during deployment, which in turn causes the deployment trigger gear 110 to rotate in a direction opposite the direction it had rotated during deployment. The ratchet rib 154 is engaged with the mode switch post 156, such that the proximal end 152 of the ratchet 140 is held off from the deployment trigger gear 110. In this way, the deployment trigger gear 110 can freely rotate back to its initial position as the deployment slide 130 is pulled proximally, without interference from the ratchet 140. The deployment slide 130 can be returned to its original position in one motion, despite the fact that it took three actuations and a final unclamping actuation of the trigger 14 to get it to its final position. As the deployment slide 130 moves proximally, the arc 53 of teeth 55 reaches a point where it moves out of engagement with the reversing gear 112, allowing the reversing gear 112 to rotate freely. When the deployment slide 130 has reached its reset position, which is the same as its initial position, the arc 53 of teeth 55 on the deployment trigger gear 110 are positioned adjacent to the reversing gear 112, ready for actuation. As set forth in the Endocutter Document, one or more feeder belts 90 may extend into the shaft 10 and/or into the handle 12 of the surgical stapler 2, such that resetting the deployment slide 130 also causes motion of those one or more feeder belts 90 in order to put fresh staples in position in the staple holder 8 for deployment.

Referring to FIGS. 6 and 15, the next step in unclamping is to slide one or both of the release buttons 13 distally. The release buttons 13 are connected to the unclamp rod 74, such that distal motion of the release button or buttons 13 causes distal motion of the unclamp rod 74. As the unclamp rod 74 moves distally, it slides along the angled-downward upper surface 78 of the unclamp aperture 76, because in the clamped mode the unclamp rod 74 is located at or near an upper surface of the unclamp aperture 76. Referring also to FIGS. 4-5, as the unclamp rod 74 slides distally along the angled-downward upper surface 78, that contact causes the clamp lock 34 to rotate about the pivot pin 60. This rotation moves the detent 102 out of contact with the clamp slide pin 100, allowing the clamp slide pin 100 to escape from the detent 102. The clamp slide 94 may be biased distally, such that when the clamp slide pin 100 escapes from the detent, it moves distally such that the clamp slide pin 100 once again is positioned against the first surface 160 of the wall or walls 35, 37 of the clamp lock 34 distal to the detent 102. This motion of the clamp slide 94 unclamps the end effector 4 in substantially the opposite manner as initial motion of the clamp slide 94 caused clamping of the end effector 4. Contact between the clamp side pin 100 and the first surface 160 moves the clamp lock tail 32 back into engagement with the ratchet tooth 148, as shown in FIG. 9. The end effector 4 is now unclamped and can be removed from the stapled tissue by the user. As another example of operation, the surgical stapler 2 may be reset by unclamping, then resetting the feeder belts 90 to place fresh staples in position for deployment. The surgical stapler 2 can now be repositioned, clamped again, and actuated again to deploy more staples.

The operation of the surgical stapler 2 may be carried out in the course of testing at a factory or other location. If so, the user that possesses the surgical stapler 2 may be a technician, machine or text fixture that exercises the surgical stapler 2 in the course of testing. The term "tissue," in the context of testing the surgical stapler 2 only, includes any substance or material used as a substitute for tissue in the course of testing.

While the invention has been described in detail, it will be apparent to one skilled in the art that various changes and modifications can be made and equivalents employed, without departing from the present invention. It is to be understood that the invention is not limited to the details of construction, the arrangements of components, and/or the method set forth in the above description or illustrated in the drawings. The use of terms such as "upward" and "downward" in this document refers to the orientation of parts on the page for descriptive clarity, and in no way limits the orientation of the device in use. Statements in the abstract of this document, and any summary statements in this document, are merely exemplary; they are not, and cannot be interpreted as, limiting the scope of the claims. Further, the figures are merely exemplary and not limiting. Topical headings and subheadings are for the convenience of the reader only. They should not and cannot be construed to have any substantive significance, meaning or interpretation, and should not and cannot be deemed to indicate that all of the information relating to any particular topic is to be found under or limited to any particular heading or subheading. Therefore, the invention is not to be restricted or limited except in accordance with the following claims and their legal equivalents.

What is claimed is:

1. Surgical apparatus, comprising:
   an end effector; and
   a handle operationally connected to said end effector, said handle including a trigger and a mode button wherein the trigger, a deployment trigger gear and a clamp trigger gear are pivotable about the mode button;
   wherein said mode button is first in a neutral position in which actuation of said trigger causes said end effector to move to a clamped configuration; and
   wherein said mode button is movable laterally to a second position in which actuation of said trigger causes said end effector to deploy staples.

2. The surgical apparatus of claim 1, wherein said mode button is biased to said neutral position.

3. The surgical apparatus of claim 1, further comprising said deployment trigger gear and said clamp trigger gear located in said handle, wherein said trigger selectively engages only one at a time of said deployment trigger gear and said clamp trigger gear; wherein engagement of said trigger with said clamp trigger gear occurs when said mode button is in said neutral position and engagement of said trigger with said deployment trigger gear occurs when said mode button is in said second position.

4. The surgical apparatus of claim 1, wherein deployment of all said staples from said end effector requires more than one actuation of said trigger.

5. Surgical apparatus, comprising:
   a handle; comprising
      a mode button;
      a trigger pivotable about said mode button;
      a ratchet pivotally connected to said trigger;
      a deployment trigger gear pivotable about said mode button; and
      a clamp trigger gear pivotable about said mode button.

6. The surgical apparatus of claim 5, wherein said ratchet includes a laterally-extending ratchet tooth, and wherein said clamp trigger gear includes a laterally-extending clamp trigger gear tooth; wherein rotation of said trigger causes rotation of said ratchet, which in turn causes said ratchet tooth to engage said clamp trigger gear tooth and cause said clamp trigger gear to rotate.

7. The surgical apparatus of claim 5, further comprising a clamp lock pivotable relative to said handle, wherein a proximal end of said clamp lock is biased downward and a distal end of said clamp lock is biased upward.

8. The surgical apparatus of claim 7, further comprising a clamp slide fixed to a clamp belt, wherein said clamp slide includes a clamp slide pin; wherein in an initial configuration said clamp slide pin is located on a first surface of said clamp lock, and wherein said clamp belt is movable to move said clamp slide pin into engagement with a detent defined on an upper surface of said clamp lock proximal to said first surface, said detent biased upward along with the remainder of the distal end of said clamp lock.

9. The surgical apparatus of claim 7, further comprising a clamp lock tail extending proximally and downward from a proximal end of said clamp lock, wherein said clamp lock tail engages a ratchet tooth in an initial configuration of said handle.

10. The surgical apparatus of claim 5, wherein said ratchet stands off from a deployment gear when said handle is in an initial configuration.

11. The surgical apparatus of claim 10, wherein a single actuation of said trigger rotates said clamp trigger gear through an arc to a clamped position, wherein said clamp trigger gear remains in said clamped position after said trigger is released.

12. The surgical apparatus of claim 11, wherein after said rotation of said clamp trigger gear to said clamped position, said mode button is actuable, after which said ratchet moves into engagement with deployment trigger gear.

13. The surgical apparatus of claim 12, further comprising a deployment belt and a deployment slide fixed to said deployment belt; wherein, after said ratchet moves into engagement with said deployment trigger gear, at least one actuation of said trigger causes rotation of said deployment trigger gear, which in turn causes said deployment belt to rotate and said deployment slide to move distally.

14. The surgical apparatus of claim 13, wherein said deployment trigger gear includes an unclamp cam along its outer perimeter, and a plurality of outer teeth.

15. The surgical apparatus of claim 13, wherein said deployment slide is manually returnable to its initial position, such that said deployment slide moves said deployment belt and in turn returns the deployment trigger gear to its initial position.

16. The surgical apparatus of claim 5, wherein said mode button is biased to a neutral position.

* * * * *